(12) United States Patent
Hawkins et al.

(10) Patent No.: US 11,395,584 B2
(45) Date of Patent: Jul. 26, 2022

(54) SURGICAL RETRACTORS

(71) Applicant: DePuy Synthes Products, Inc., Raynham, MA (US)

(72) Inventors: John Riley Hawkins, Cumberland, RI (US); Nicholas Pavento, North Attleboro, MA (US); Sean P. Selover, Westport, MA (US); Michelle LeClerc, Middleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 355 days.

(21) Appl. No.: 16/517,536

(22) Filed: Jul. 19, 2019

(65) Prior Publication Data

US 2019/0335990 A1 Nov. 7, 2019

Related U.S. Application Data

(63) Continuation of application No. 14/797,717, filed on Jul. 13, 2015, now Pat. No. 10,398,299, which is a (Continued)

(51) Int. Cl.
*A61B 1/32* (2006.01)
*A61B 1/06* (2006.01)
(Continued)

(52) U.S. Cl.
CPC .............. *A61B 1/32* (2013.01); *A61B 1/06* (2013.01); *A61B 1/0684* (2013.01); *A61B 1/07* (2013.01);
(Continued)

(58) Field of Classification Search
None
See application file for complete search history.

(56) References Cited

U.S. PATENT DOCUMENTS

| 3,888,117 A | 6/1975 | Lewis |
| 4,784,150 A | 11/1988 | Voorhies et al. |

(Continued)

FOREIGN PATENT DOCUMENTS

| JP | H10-277043 A | 10/1998 |
| JP | 2007-514501 A | 6/2007 |

(Continued)

OTHER PUBLICATIONS

Japanese Office Action for Application No. 2019-070372, dated Jan. 12, 2021 (9 pages).
(Continued)

*Primary Examiner* — Tessa M Matthews
(74) *Attorney, Agent, or Firm* — Barnes & Thornburg LLP

(57) ABSTRACT

The present disclosure relates to methods and devices for surgically manipulating tissue. In general, the methods and devices can include an elongate retractor shaft having a distal retractor tip that is configured to manipulate tissue, for example the tip can be configured to separate muscle and nerve fibers surrounding a vertebra. The elongate retractor shaft can include an illumination source such that at least a portion of the surgical field is illuminated by the device when the device is used in the body. A sensor can also or alternatively be included on the elongate retractor shaft, for example on the blunt retraction tip, such that the sensor can monitor physiological parameters of the tissue in or adjacent to the surgical field.

19 Claims, 13 Drawing Sheets

Related U.S. Application Data continuation of application No. 13/832,727, filed on Mar. 15, 2013, now Pat. No. 9,125,587.

(51) Int. Cl.

| | | |
|---|---|---|
| *A61B 17/02* | (2006.01) | |
| *A61B 1/07* | (2006.01) | |
| *A61B 5/00* | (2006.01) | |
| *A61B 5/01* | (2006.01) | |
| *A61B 5/145* | (2006.01) | |
| *A61B 90/00* | (2016.01) | |
| *A61B 5/24* | (2021.01) | |
| *A61B 17/00* | (2006.01) | |
| *A61B 90/30* | (2016.01) | |

(52) U.S. Cl.
CPC ............ *A61B 5/01* (2013.01); *A61B 5/14542* (2013.01); *A61B 5/24* (2021.01); *A61B 5/6847* (2013.01); *A61B 5/746* (2013.01); *A61B 17/02* (2013.01); *A61B 17/025* (2013.01); *A61B 17/0206* (2013.01); *A61B 17/0218* (2013.01); *A61B 90/06* (2016.02); *A61B 5/14503* (2013.01); *A61B 5/14539* (2013.01); *A61B 5/14546* (2013.01); *A61B 17/0293* (2013.01); *A61B 90/36* (2016.02); *A61B 2017/00092* (2013.01); *A61B 2017/00473* (2013.01); *A61B 2017/00946* (2013.01); *A61B 2017/0225* (2013.01); *A61B 2017/0262* (2013.01); *A61B 2090/064* (2016.02); *A61B 2090/065* (2016.02); *A61B 2090/309* (2016.02)

(56) References Cited

U.S. PATENT DOCUMENTS

| | | | |
|---|---|---|---|
| 4,945,896 A | 8/1990 | Gade | |
| 5,769,781 A * | 6/1998 | Chappuis | A61B 17/02 |
| | | | 600/201 |
| 5,928,137 A | 7/1999 | Green | |
| 6,139,489 A | 10/2000 | Wampler et al. | |
| 7,166,073 B2 | 1/2007 | Ritland | |
| 8,055,349 B2 | 11/2011 | Gharib et al. | |
| 8,202,216 B2 | 6/2012 | Melkent et al. | |
| 8,382,666 B1 | 2/2013 | Mao et al. | |
| 9,125,587 B2 | 9/2015 | Hawkins et al. | |
| 10,398,299 B2 | 9/2019 | Hawkins et al. | |
| 2003/0088157 A1 | 5/2003 | Vassiliades et al. | |
| 2005/0080320 A1 | 4/2005 | Lee et al. | |
| 2005/0113654 A1 | 5/2005 | Weber et al. | |
| 2005/0131457 A1 | 6/2005 | Douglas et al. | |
| 2006/0094931 A1 * | 5/2006 | Danitz | A61M 25/0105 |
| | | | 600/141 |
| 2006/0256575 A1 | 11/2006 | Vayser | |
| 2007/0010716 A1 | 1/2007 | Malandain et al. | |
| 2007/0066872 A1 * | 3/2007 | Morrison | A61B 17/02 |
| | | | 600/212 |
| 2007/0208226 A1 | 9/2007 | Grey et al. | |
| 2007/0244489 A1 | 10/2007 | Patel et al. | |
| 2008/0319290 A1 | 12/2008 | Mao et al. | |
| 2009/0105605 A1 | 4/2009 | Abreu | |
| 2009/0137887 A1 | 5/2009 | Shariati et al. | |
| 2009/0163943 A1 | 6/2009 | Cavanaugh et al. | |
| 2010/0174146 A1 * | 7/2010 | Miles | A61B 1/32 |
| | | | 600/202 |
| 2011/0077466 A1 | 3/2011 | Rosenthal | |
| 2011/0077668 A1 | 3/2011 | Gordon et al. | |
| 2011/0112570 A1 | 5/2011 | Mannava et al. | |
| 2011/0144640 A1 | 6/2011 | Heinrich et al. | |
| 2011/0144687 A1 | 6/2011 | Kleiner | |
| 2011/0184245 A1 | 7/2011 | Xia et al. | |
| 2011/0190588 A1 | 8/2011 | McKay | |
| 2011/0257478 A1 | 10/2011 | Kleiner et al. | |
| 2011/0301421 A1 | 12/2011 | Michaeli et al. | |
| 2012/0059226 A1 | 3/2012 | Funt | |
| 2012/0116170 A1 | 5/2012 | Vayser et al. | |
| 2012/0245431 A1 * | 9/2012 | Baudouin | A61B 17/0218 |
| | | | 600/213 |
| 2014/0088367 A1 * | 3/2014 | DiMauro | A61N 5/0622 |
| | | | 600/202 |
| 2014/0275792 A1 | 9/2014 | Hawkins et al. | |
| 2014/0277323 A1 | 9/2014 | Tingey | |
| 2014/0343358 A1 | 11/2014 | Hameed et al. | |
| 2015/0313456 A1 | 11/2015 | Hawkins et al. | |

FOREIGN PATENT DOCUMENTS

| | | |
|---|---|---|
| JP | 2011-523368 A | 8/2011 |
| JP | 2016-521997 A | 7/2016 |
| WO | 2007/085909 A2 | 8/2007 |
| WO | 2007/121271 A2 | 10/2007 |

OTHER PUBLICATIONS

Japanese Office Action for Application No. 2019-070372, dated Jun. 15, 2021 (5 pages).
No Author Listed SynFrame Access and Retractor System Assembly Guide. Synthes Spine. Aug. 2010. (12 pages).
International Search Report for PCT/US14/018988 dated Sep. 8, 2014 (6 pages).
U.S. Appl. No. 13/832,727, filed Mar. 15, 2013, Surgical Retractors.
U.S. Appl. No. 14/797,717, filed Jul. 13, 2015, Surgical Retractors.

\* cited by examiner

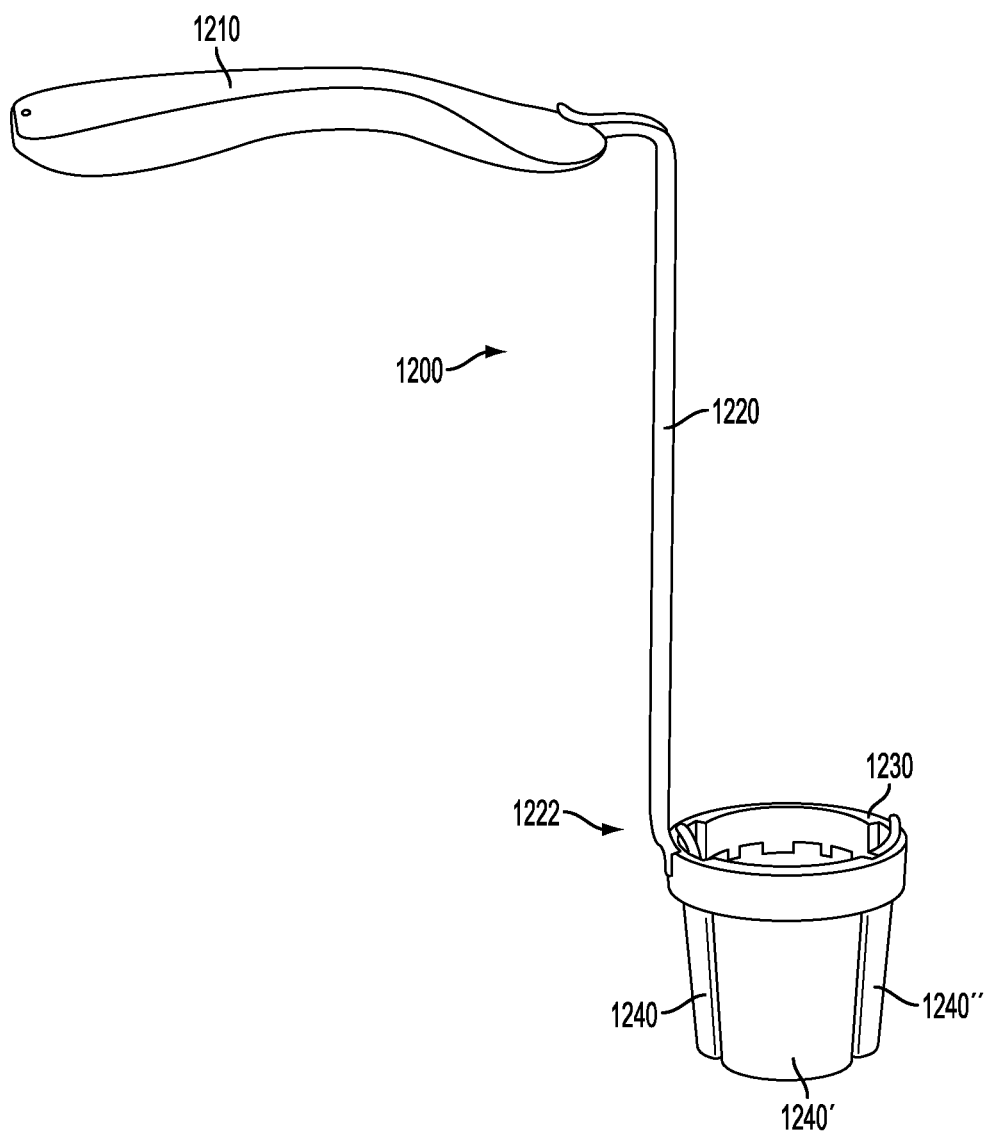

SURGICAL RETRACTORS

CROSS-REFERENCE TO RELATED APPLICATIONS

This application is a continuation of U.S. application Ser. No. 14/797,717, filed Jul. 13, 2015, entitled "Surgical Retractors." U.S. application Ser. No. 14/797,717 is a continuation of U.S. application Ser. No. 13/832,727, filed on Mar. 15, 2013, entitled "Surgical Retractors," and now issued as U.S. Pat. No. 9,125,587. The entire contents of each of these applications is incorporated by reference herein.

FIELD

The present disclosure relates generally to surgical retractor devices and methods for manipulating tissue.

BACKGROUND

Surgical procedures for accessing tissue located deep within the body can pose a risk of trauma to the intervening tissue, particularly when the tissue includes neural tissue. During a surgical procedure where access to the spine is required, the final layers of tissue, those most proximate to the spine, are densely populated with large nerve fibers. Since the tissue is nerve-dense, the surgeon must take the greatest care when manipulating the tissue as the deep nerve fibers are remote from the surgeon, follow only general anatomic patterns, and are beneath, within, or above sensitive layers of tissue.

Various configurations of access devices have been developed to gain and maintain access to surgical fields, such as the spinal column, through deep access portals in tissue. For example, Penfield devices have been used in surgical procedures to manipulate muscular and neural tissue. However, the use of a Penfield device requires extending the tip of the Penfield device deep into the access portal to the surgical field. As the Penfield device is disposed within the deep access cavity, the surgeon typically losses visual contact of tissue that is adjacent to the distal tip of the Penfield device. As the surgeon loses sight of the working area, often due to a lack of light in the deep access portal, the likelihood of inadvertent contact and damage of sensitive neural tissue increases.

Accordingly, there remains a need for improved methods and devices for safely performing the surgical retraction of tissue.

SUMMARY

Devices and method are provided for surgically manipulating tissue, such as muscle fibers, including embedded neural tissue within a deep access portal in a body. Specifically, the methods and devices described herein can provide an effective means to manipulate tissue with an increased field of vision for a surgeon. The methods and devices can also provide for monitoring of physical parameters.

In one embodiment, a surgical device for surgically manipulating tissue is provided and can include an elongate retraction shaft having a proximal end with a handle portion, and a distal end having a blunt retraction tip configured to retract tissue within a body without appreciably severing the tissue. The surgical device can also include an illumination source disposed on the elongate retraction shaft and configured to illuminate at least a portion of tissue being manipulated by the retraction tip. Furthermore, the device can have a sensor disposed on the retraction tip that can be configured to sense at least one physiological parameter of tissue being manipulated by the retraction tip. A connector can be coupled to the handle and electrically coupled to at least one of the illumination source and the sensor.

In one embodiment, the connector can be electrically coupled to the sensor and it can be configured to transfer a signal between the sensor and an external signal processor. The device can include an internal power source disposed within the handle portion that can be configured to provide power to at least one of the illumination source and the sensor.

The blunt retraction tip can have a variety of configurations. In one embodiment, the tip can have a concave surface configured to conform to a bone surface. The elongate retraction shaft can be linear or in other embodiments it can be non-linear with at least one bend formed therein such that the blunt retraction tip extends along a central longitudinal axis that is transverse to a central longitudinal axis of the handle portion. In certain embodiments the blunt retraction tip is in the shape of a dissector, such as a Penfield dissector. The elongate retraction shaft can have a lumen extending through at least a portion thereof. In certain embodiments, the connector can extend through the lumen, the illumination source can be at least partially disposed within the lumen, and/or the sensor can be at least partially disposed within the lumen. In some embodiments, the sensor can be laminated to an external surface of the elongate retraction shaft or molded/inserted within the retraction shaft and exposed at a distal portion thereof. Embodiments of an elongate retraction shaft having at least a portion that is malleable are also provided.

The illumination source can include a light emitting diode. While the location can vary, in one embodiment, the illumination source can be disposed proximally adjacent to the retraction tip. The sensor can also have various configurations and can be configured to sense at least one physiological parameter such as temperature, pressure, blood oxygen level, neuro conductivity, or combinations thereof. In another embodiment, the retraction tip can be removably coupled to the elongate retraction shaft.

In one embodiment, a signal processor can be disposed within the handle portion and coupled to the connector. The signal processor can be configured to monitor the at least one physiological parameter and to communicate to a user when the parameter falls outside of a preset range.

In another embodiment, a surgical system for manipulating tissue within a body is provided and includes a handle having an elongate shaft extending distally therefrom. The system can include a support ring coupled to a distal end of the elongate shaft. The system can also have a plurality of blades removably mated to the support ring and configured to retract tissue. An illumination source can be disposed on at least one of the elongate shaft and the support ring and the illumination source can be configured to illuminate tissue being retracted. The system can include a sensor disposed on at least one of the elongate shaft, the support ring, and the plurality of blades and configured to monitor at least one physiological parameter of a body tissue. In one embodiment, the plurality of blades can be configured to snap-fit onto the support ring.

A surgical kit is also provided. In one embodiment, the kit can include at least one retractor having a proximal end, a distal end, and an illumination source to illuminate an area surrounding the distal end. The distal end can have a blunt dissecting tip and a sensor disposed thereon to monitor at least one physiological parameter of a body tissue. The kit can also include at least one modular tip configured to be disposed over the blunt dissecting tip of the at least one retractor, and at least one support ring configured to support the retractor at the proximal end of the retractor when the retractor is disposed within the body.

BRIEF DESCRIPTION OF DRAWINGS

This invention will be more fully understood from the following detailed description taken in conjunction with the accompanying drawings, in which:

FIG. 8C is a perspective view of the ring retractor of FIG. 8A shown with only three blades mated thereto;

DETAILED DESCRIPTION

Figure 1A:
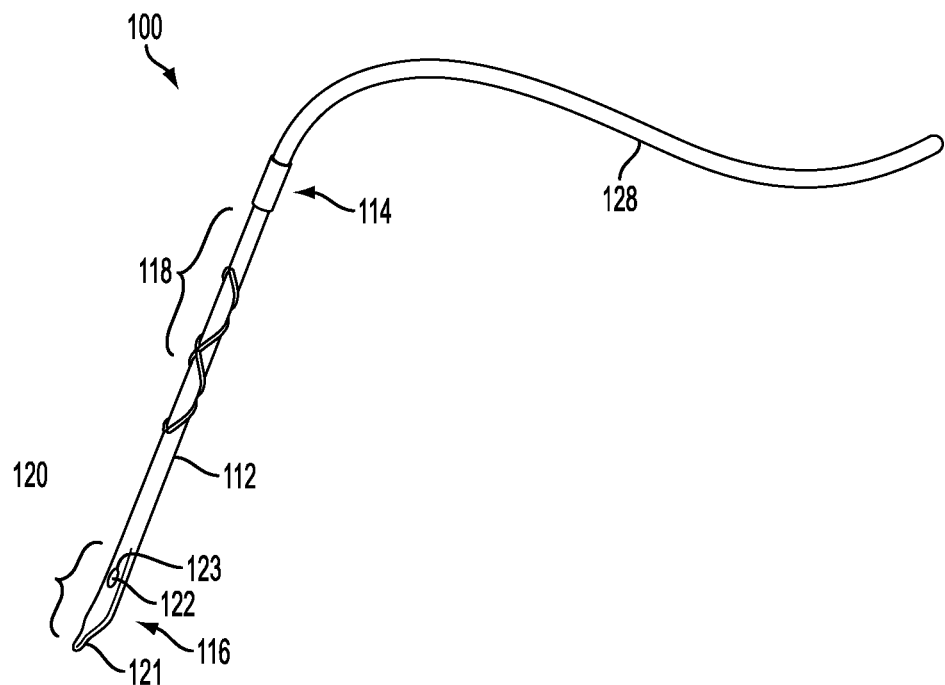
FIG. 1A is a perspective view of one embodiment of a tissue retractor.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, like-numbered components of the embodiments disclosed herein generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Minimally invasive surgical procedures have been developed to minimize the risk of trauma to surrounding tissue during surgical procedures. For example, lateral approach thoracic surgery is now a common method of performing spinal surgery. However, in performing minimally invasive surgeries, visibility of the surgical field is significantly reduced, thus leading to an increased risk of traumatic contact with neural tissue. Thus, to safely and reliably perform surgical procedures, such as lateral approach thoracic procedures, increased fields of vision and monitoring capabilities are necessary.

The present invention relates to methods and devices for surgically manipulating tissue, such as muscle fibers including embedded neural tissue within a deep access portal in a body. In general, the methods and devices include an elongate retractor shaft having a distal retractor tip that is configured to manipulate tissue, for example the tip can be configured to separate muscle and nerve fibers surrounding a vertebra. The elongate retractor shaft can include an illumination source such that at least a portion of the surgical field is illuminated by the device when the device is used in the body. A sensor can also or alternatively be included on the elongate retractor shaft, for example on the blunt retraction tip, such that the sensor can monitor physiological parameters of the tissue in or adjacent to the surgical field. The device can include various features to allow for mating with support structures, retraction of tissue, modularity, etc., exemplary embodiments of which are discussed in detail below. A person skilled in the art will appreciate that a device can have any combination of features disclosed herein. The devices disclosed herein can also be configured for use in any procedure in which it is necessary to manipulate tissue, including both open surgery and minimally invasive procedures. In certain exemplary embodiments, the methods and devices disclosed herein can be particularly useful in minimally invasive procedures where access to the surgical field is through a small portal or cannula with limited vision. As mentioned, one such use is in spinal surgeries, such as minimally invasive lateral approach thoracic procedures.

Figure 1B:
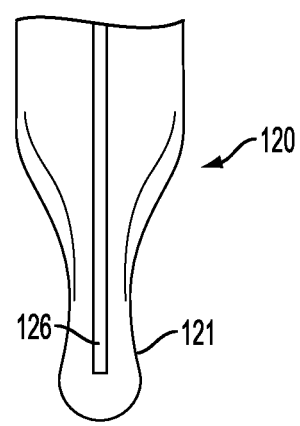
FIG. 1B is a perspective view of the distal end of the retractor of FIG. 1A.

FIGS. 1A and 1B illustrate one embodiment of the surgical retraction device 100. As shown, the surgical retraction device 100 is in the form of a generally elongate retraction shaft 112 having a proximal end 114 and a distal end 116. The proximal end 114 can include a handle portion 118 configured to be grasped by a user, and the distal end 116 can include a tissue retraction tip 120. An illumination source 122 can be disposed on the elongate retraction shaft 112 for illuminating tissue surrounding the device. The device 100 can also include a sensor 126 disposed thereon and configured to monitor physiological parameters, e.g., neural and myo monitoring, temperature, pressure, and blood oxygen levels, of the tissue contacted by the tip. A connector 128 can be coupled to the proximal end 114 of the device and it can be electrically or fiber optically coupled to at least one of the illumination source 122 and the sensor 126. In some embodiments, the connector 128 can be formable to hold the retractor in place.

As indicated above, the proximal end 114 of the elongate retraction shaft 112 can include a handle portion 118 that is configured to be grasped by a surgeon. The handle portion 118 can have any shape and size, and it can merely be a portion of the shaft configured to be grasped. In the illustrated embodiment, the handle portion 118 includes gripping features, which can be in the form of one or more ridges or surface protrusions extending around the shaft, to facilitate grasping by a user. The ridges can also facilitate mating of the device to a support member, such as a snap-fitting on a support ring. In other embodiments, a handle can be formed on or coupled to the shaft and it can have an ergonomic shape designed to allow a user to grip the device 100 comfortably while allowing for optimum manipulation of the blunt retraction tip 120. While not shown in FIG. 1A, the handle portion 118 can also include features for facilitating mating to another device, such as a support ring, wrench, or a robotic arm. For example, the handle portion 118 can include a central aperture that allows for attachment to a mechanical arm or device.

The handle portion 118 can also include a variety of other features, such as a display for communicating sensed physiological parameters of the tissue being manipulated, or for displaying tissue imaged by a distal end of the device. In other embodiments, the handle portion 118 can be configured to couple to various external devices, such as an image guidance system or an external power supply. In another embodiment, the handle portion 118 can house an internal power supply, such as a battery, and any electrical circuitry required to control and power the illumination source 122 and/or the sensor 126. For example, the circuitry can include an internal signal processor for monitoring the sensor 126 signal. While not shown, the handle portion 118 can also include a switch for allowing a user to activate at least one of the illumination source and the sensor. Various switches known in the art can be used.

The elongate shaft 112 extends distally from the handle portion 118 and is preferably dimensioned so as to allow the distal end 116 of the elongate retraction shaft to be disposed within a body cavity for manipulating tissue, while the proximal end 114 is positioned outside of the patient's body for allowing the handle portion 118 to be grasped by a user. While the length can vary depending on the intended use, in one embodiment the length of the elongate shaft 112 can be in the range of about 30 mm to about 200 mm. The diameter of the shaft, as well as the diameter of the handle portion 118, can vary depending on the intended use, and the shaft and handle can have the same or different diameters. In one embodiment, the handle portion 118 can have a diameter that is greater than a diameter of the shaft 112 to facilitate gripping of the device. By way of non-limiting example, the diameter of the handle can be in the range of about 5 mm to about 25 mm, and the diameter of the shaft can be in the range of about 3 mm to about 12 mm. The shaft 112 can also be generally rigid and linear, extending along a single longitudinal axis, or in other embodiments the shaft can be non-linear and/or flexible or malleable.

As indicated above, the retraction tip 120 is formed on the distal end 116 of the elongate shaft 112. The retraction tip 120 can have various configurations for manipulating tissue in the body, and the particular configuration can depend on the intended use. For example, the retraction tip 120 can be in the form of a blunt tip configured to allow a surgeon to separate muscle and neural fibers near the spinal column and to retract and retain the tissue out of the surgical field giving access to vertebral bone tissue under the retracted muscle and neural tissue, such as a Penfield dissector as known in the art. In the illustrated embodiment, the retraction tip 120 can have a generally flattened configuration such that a width extending in a first direction perpendicular to a longitudinal axis of the shaft is greater than a depth extending in a second opposite direction perpendicular to the longitudinal axis. The generally flattened tip can have a distal-most portion with a reduced diameter so as to form a pointed cylindrical tip portion 121. In other embodiments, however, the retraction tip can be cylindrical, concave along any one or more surfaces, rectangular, spherical, etc. The tip can include a groove or central lumen to aid in the positioning of additional tools such as a surgical wire or a fixation pin. The tip can be sufficiently narrow to penetrate and anchor in a bone surface with the aid of a surgeon or it can be anchored with a screw or pin. The central lumen can also be used to provide aspiration when a vacuum source is connected to the handle 128. Additionally, the blunt retraction tip 120 can be configured to removably mate to the elongate shaft and a plurality of modular tips having various shapes and sizes can be provided, as will be discussed in detail below.

As mentioned above, the retractor 100 can also include an illumination source 122 for illuminating tissue surrounding the distal retraction tip 120. The illumination source can include a plurality of light sources, for example two light emitting diodes. Alternatively, the illumination source can be a singular light source. The illumination source can produce a diffuse light field radiating from the light source so as to light the general working area. Alternatively, the illumination source can be configured to produce a targeted light field that shines directly onto a desired area, for example the illumination source can be directed to shine toward the cylindrical tip portion 121 of the retractor 100. In some embodiments, the targeted light field is the result of divergent or convergent configuration of the illumination sources balancing the light about the tip portion and the adjacent tissue. The illumination source can be any known light source that is capable of providing illumination to a cavity. For example, the illumination source can be a light emitting diode, an organic light emitting diode, a fiber optic lighting system such as those including polymeric light pipes, and/or chemical luminescent strips.

The illumination source can be disposed at any location along the elongate shaft 112 such that when the device is disposed within a patient's body, e.g., within a deep access portal, the illumination source will illuminate at least a portion of the surgical field, such as tissue surrounding a vertebra. The location of the illumination source can vary depending on the quantity of illumination sources as well as the intended use. In the embodiment shown in FIG. 1A, the illumination source 122 is positioned proximally adjacent to the distal end 116, and more particularly proximal to the cylindrical tip portion 121. This will allow the illumination source 122 to illuminate tissue being manipulated by the retraction tip 120. A person skilled in the art will appreciate that the illumination source 122 can be positioned at any location along the length of the shaft 112, including along the handle portion 118 or at the cylindrical tip portion 121. Moreover, the device 100 can include multiple illumination sources. In certain exemplary embodiments, the illumination source 122 is positioned a distance from the distal-most end of the shaft 121 that is in the range of about 10 mm to about 100 mm.

The illumination source can be coupled to the retractor device 100 using a variety of techniques. In the illustrated embodiment, the illumination source 122 is in the form of a light emitting diode that is disposed within a bore 123 formed in the shaft 112. While not shown, the bore can extend into an inner lumen that extends through the shaft 112 for allowing the illumination source 122 to be coupled to a power source disposed within the handle, or through an electrical connector 128 extending from a proximal end of the handle portion 118. In some embodiments, the illumination source 122 can be fiber optically connected with connector 128.

As indicated above, the device 100 can also include a sensor for sensing one or more physiological parameters of tissue being manipulated by the retraction tip 120. FIG. 1B illustrates the retraction tip 120 of the device 100 in more detail. While the sensor 126 can be positioned at various locations along the shaft 112, in the illustrated embodiment the sensor 126 is disposed on an external surface and extends longitudinally along the retraction tip 120 such that the sensor 126 will come into contact with tissue being manipulated. The sensor 126 can be disposed on the same side or on an opposite side of the shaft 112 as the illumination source 122. The sensor 126 can be mated to the retraction tip 120 for instance by laminating the sensor 126 to the distal end 116. Alternatively, the sensor 126 can be disposed within a bore or lumen in the blunt retraction tip 120, or a portion of the tip itself can configured to function as a sensor, for example surfaces of the retraction tip 120 can function as a thermocouple to measure temperature. In some embodiments, the retraction tip 120 can include a single sensor to monitor a single parameter, multiple sensors for monitoring a number of different parameters, or a single sensor that can monitor more than one parameter. In use, the sensor(s) can be configuration to measure a variety of physiological parameters, as will be discussed in more detail below.

Figure 2:
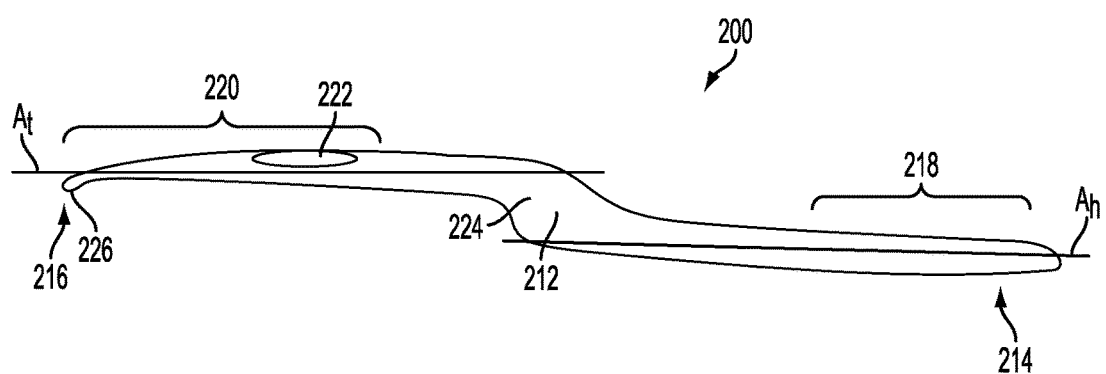
FIG. 2 is a side view of one embodiment of a tissue retractor having an S-shaped bend in the shaft.

FIG. 2 illustrates another embodiment of a tissue retractor 200, which can be similar to the retractor 100 of FIG. 1, but which has a non-linear shaft 212. As shown, the retractor 200 generally includes a handle portion 218 at a proximal end 214 of the shaft 212 and a retractor tip 226 at a distal end 216 of the shaft. The retractor 200 also includes an illumination source 222 disposed on the shaft 212 at a location proximally adjacent to the distal retractor tip 226. While not shown, the retractor can further include a sensor, as discussed above with respect to FIG. 1.

As indicated above, in this embodiment the retractor shaft 212 is non-linear. While the non-linear shape can vary and the shaft 212 can include any number of bends or curves formed therein, in the illustrated embodiment the shaft includes an S-shaped bend 224 formed at a general mid-portion thereof. This S-shaped bend 224 preserves a surgeon's line of sight to the tip 226 by having the handle portion 218 extend along a longitudinal axis $A_h$ that is offset from along a longitudinal axis $A_t$ of the portion containing the retractor tip 226. The surgeon's view is thus unobstructed by the surgeon's hands or other support structure supporting the handle portion 218. The elongate retractor shaft can optionally be malleable such that the location of any bends can be adjusted and the shaft can be oriented in a desired configuration. In other embodiments, the shaft can be formed from a shape-memory material such that the curvature changes in response to change in temperature or other outside stimulus.

Figure 3:
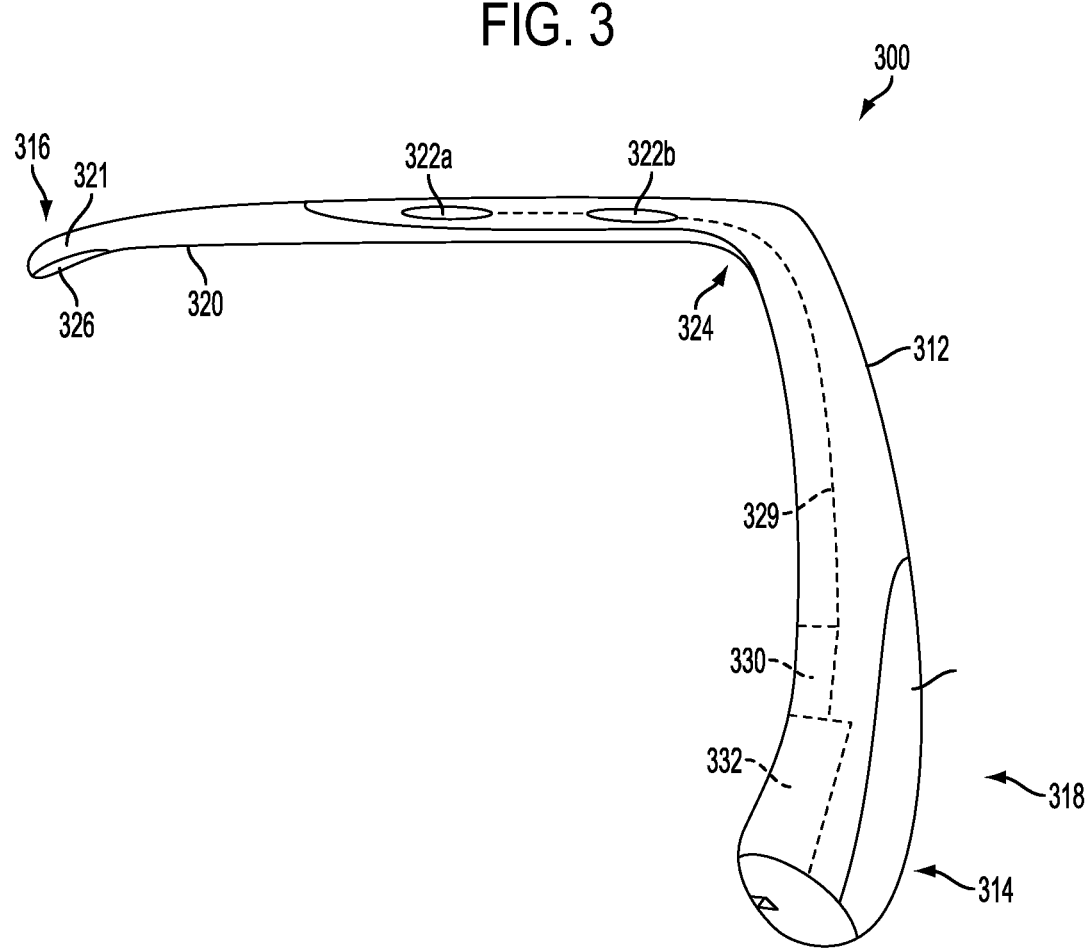
FIG. 3 is side view of one embodiment of a tissue retractor having an L-shaped bend in the shaft.

FIG. 3 illustrates another embodiment of a tissue retractor 300 having a handle portion 318 and a non-linear elongate retractor shaft 312 extending distally from the handle 318. In this embodiment, the handle 318 is shown having a switch 334, a power source 332, a signal processor 330, and a connector 329 extending between the signal processor 330 and a sensor 326 located in the retraction tip 320, and more particularly in the distal-most tip 321. The power source 332 can be in the form of a battery and the switch 334 can be coupled to the battery and to the signal processor 330. As a result, when the switch 334 is activated, power is delivered from the power source 332 to the signal processor 330, which in turn sends a signal through the connector 329 to at least one of the sensor 326 and first and second illumination sources 322*a*, 322*b*. FIG. 3 furthers illustrates an L-shaped bend 324 formed at a substantial mid-portion of the shaft 312 between proximal and distal ends 314, 316 thereof. As a result, a longitudinal axis through the retraction tip 320 is substantially transverse to a longitudinal axis through the handle portion 318.

Figure 4:
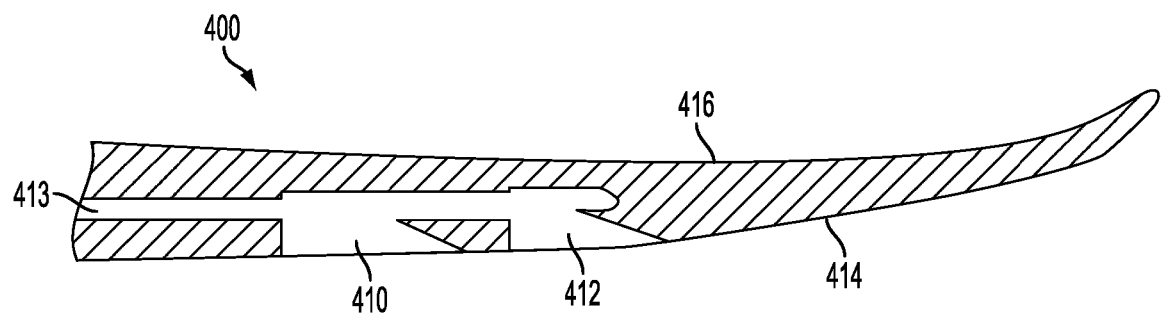
FIG. 4 is a cross-sectional view of a distal end of another embodiment of a tissue retractor.

FIG. 4 illustrates a distal portion of another embodiment of an elongate retractor shaft 400 having a first aperture 410 and a second aperture 412 formed in the retractor shaft through which first and second illumination sources (not shown) can be at least partially disposed. As further shown in FIG. 4, the shaft 400 can include an inner lumen 413 extending therethrough for receiving one or more electrical or fiber optic connectors (not shown) for connecting the illumination sources to a power source or fiber optic system. In this embodiment, the apertures 410, 412 are formed in a first surface 414 having a substantially convex shape, and the retraction shaft 400 includes a second, opposite surface 416 that is substantially concave. The illumination sources can be seated within the apertures 410, 412 and retained therein using various techniques, such as threads, adhesives, welding, etc. Alternatively, the illumination source can be laminated onto an outer surface 414, 416 of the elongate retraction shaft.

Figure 5:
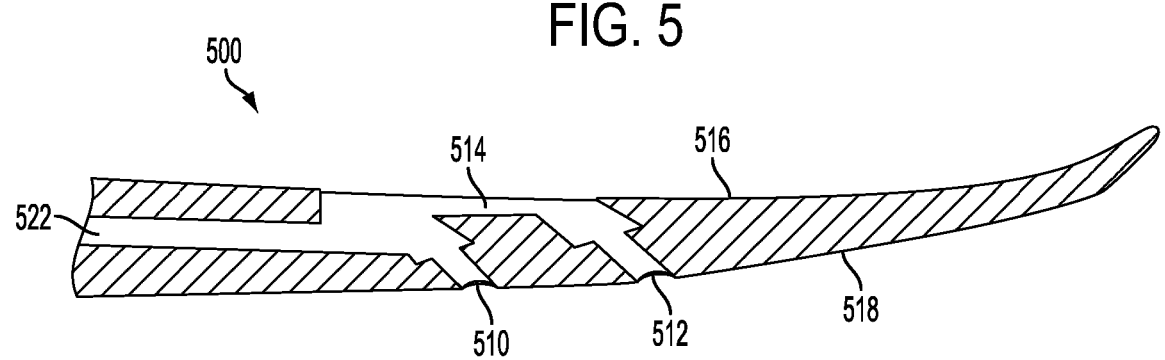
FIG. 5 is a cross-sectional view of a distal end of another embodiment of a tissue retractor.

FIG. 5 illustrates a distal portion of another embodiment of an elongate retractor shaft 500 having a first aperture 510 and a second aperture 512 formed in a first substantially convex surface 518 of the retractor shaft 500. The first aperture 510 and second aperture 512 can be configured to seat first and second illumination sources (not shown). In some embodiments, the retractor shaft 500 can have another, third aperture 514 on a second or opposite substantially concave surface 516. One or more additional illumination sources can be disposed within the third aperture 514 for illuminating tissue in a direction opposite to the direction of illumination provided by the illumination sources disposed within the first and second apertures 510, 512. As with the previous embodiment, the elongate shaft 500 can include a lumen 522 extending therethrough and configured to provide access, e.g., for one or more electrical or fiber optic connectors, from a proximal end (not shown) of the shaft 500 to the apertures 510, 512, 514.

As indicated above, in some embodiments, such as those shown in FIGS. 4 and 5, the lumen 413, 522 extending therethrough can house an electrical coupling for the illumination source. Additionally or alternatively, the lumen 413, 522 can house a fiber optic coupling for the illumination source. The lumen can extend from the proximal end of the elongate shaft to the distal end, or can only extend through a portion of the shaft, e.g., terminating proximal to the distal-most end. The lumen can be so dimensioned as to allow an electrical or fiber optic coupling to extend from the proximal end of the shaft to the illumination source, the sensor, or both. Additionally, the shaft can have more than one lumen, for instance the shaft can include a first lumen housing a first electrical coupling and a second lumen designed to deliver surgical accessories or tools, such as bone screws, to the surgical field (not shown). Additionally, the second lumen can also be configured to provide aspiration with a vacuum system. The electrical coupling can be any known coupling mechanism, such as a conductive wire.

Figure 6:
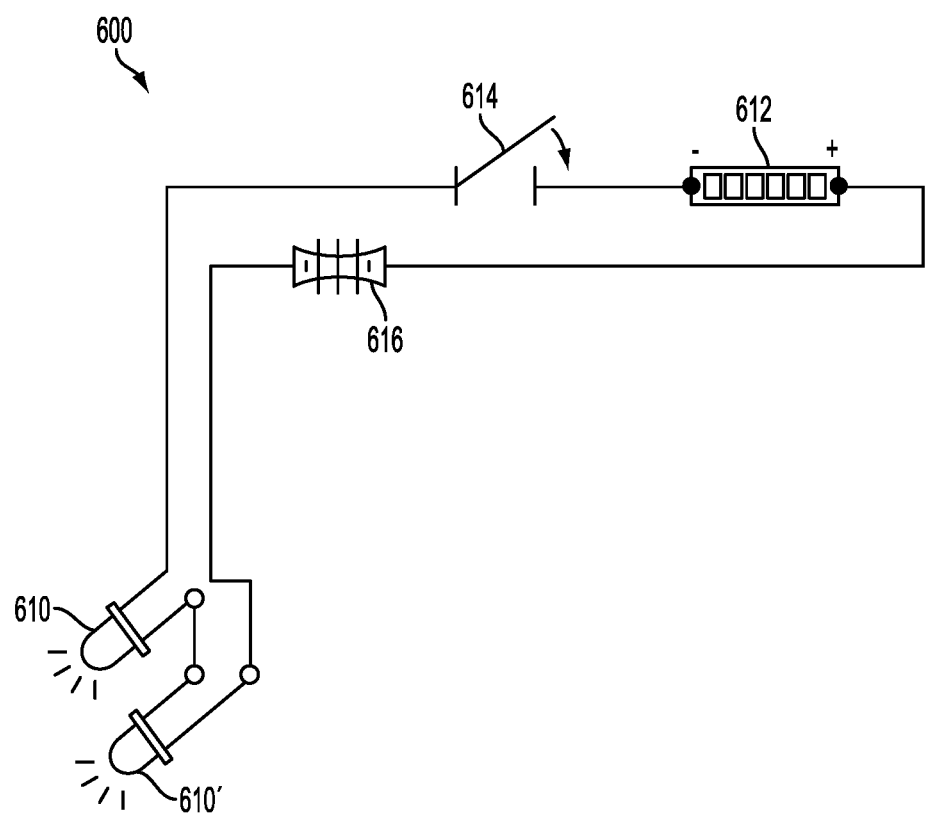
FIG. 6 is a schematic of one embodiment of an illumination source power circuit.

FIG. 6 illustrates an exemplary circuit 600 to power first and second illumination sources 610, 610'. The illumination sources 610, 610' can be powered by an internal power source 612. The power source 612 can be disposed on or within the device, for instance in a cavity within the handle (for example in FIG. 3, power source 332 is disposed within handle 312). Alternatively, the power source 612 can be external to the device and electrically connected to the proximal end of the handle through a connector, such as an electrical cord or cable as shown in FIG. 1. The power source 612 can include a battery or series of batteries as is known in the art or can include any other known power source, such as a standard wall outlet.

As shown in FIG. 6, the power source 612 can be electrically coupled to the illumination sources 610, 610' by a circuit 600 that includes a switch 614 and a fuse or diode 616. The switch 614 can be configured to control power to the illumination source 610, 610' such that a user can control the optical output of the illumination source 610, 610'. The switch 614 can be any mechanism capable of controlling power to the illumination source 610, 610', including on/off switches or dimmer-type switches to give a range of light outputs. In one embodiment, the switch 614 can be a physical switch disposed on the handle that is configured to be manipulated by a surgeon. For example, the switch 614 can be a touch-sensitive surface that is toggled as a surgeon touches any portion of the surface of the handle (for example, the switch 334 in FIG. 3). In other embodiments, the switch 614 can be a depressible button-type switch disposed on the handle. In some embodiments, the switch 614 can be a one-way on switch that is activated as soon as the device is removed from a sterile package (not shown).

Figure 7A:
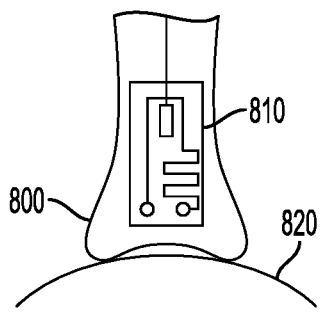
FIG. 7A is a partial schematic of one embodiment of a lab-on-a-chip sensor disposed on a retractor tip.
Figure 7B:
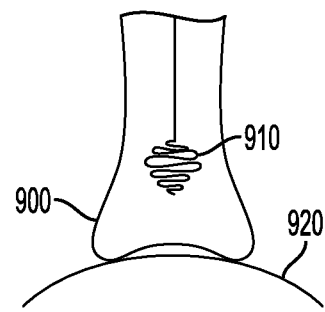
FIG. 7B is a partial schematic of one embodiment of a pressure sensor disposed on a retractor tip.
Figure 7C:
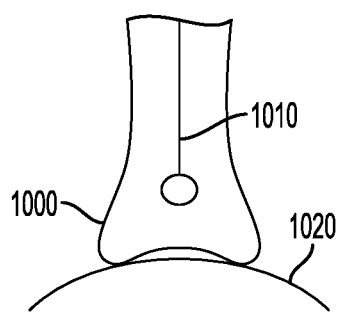
FIG. 7C is a partial schematic of one embodiment of a temperature sensor disposed on a retractor tip.
Figure 7D:
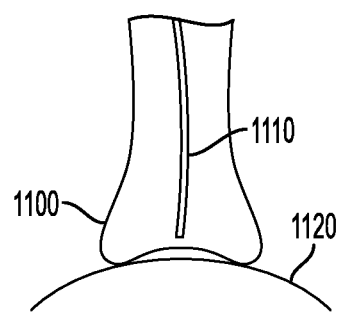
FIG. 7D is a partial schematic of one embodiment of a conductivity sensor disposed on a blunt retractor tip.

FIGS. 7A-7D illustrate various types of exemplary sensors for use on any of the retraction tips disclosed herein. The sensor can be configured to measure any parameter that has physiological significance to one skilled in the art. For example, the physiological parameters monitored by exemplary sensors can include temperature, pressure, blood oxygen levels, and electrical conductivity. As shown in FIG. 7A, the sensor 810 is in the form of a lab-on-a-chip sensor 810 that is disposed on a retractor tip 800 having a generally concave distal-facing surface so as to conform to bone 820 as shown. The lab-on-a-chip sensor can be as small as a few millimeters and can utilize micro fluidics to analyze physiological parameters of the adjacent tissue. For example, a lab-on-a-chip sensor can monitor the blood oxygen levels in the adjacent tissue. FIG. 7B illustrates another tip 900 having a concave surface that conforms to a surface of a bone 920. The sensor 910 in this embodiment is a pressure sensor 910 for sensing applied pressure. The pressure sensor can be any type of pressure sensor known in the art, for example a force sensing resistor, resistive strain gauge, dielectric pressure sensitive film, piezoelectric type sensor, capacitive, electromagnetic, potentiomatic, resonant, and thermal type pressure sensors. In another embodiment, shown in FIG. 7C, tip 1000 includes a temperature sensor 1010, such as a thermocouple. As with the tips shown in FIGS. 7A and 7C, tip 1000 includes a distal-facing concave surface configured to conform to bone 1020. FIG. 7D illustrates yet another embodiment of a tip 1100 that is configured to have a concave surface that conforms to a surface of a bone 1120. In this embodiment, the sensor is in the form of an electrical conductivity meter 1110, such as that commonly used in neural and myo monitoring systems.

The various sensors disclosed herein can be configured to monitor real-time data during a surgical process and can be coupled to computational devices such that a surgeon can be alerted if the monitored parameter is outside of a preset range. Computational devices can include known patient monitoring systems that are in an operating room or procedure room, or alternatively or additionally can include a signal processor and computational device stored directly in the elongate retraction shaft of a retractor device. If stored directly in the shaft, the computational device or signal processor can be disposed anywhere in the shaft (for example, as shown in FIG. 3, the signal processor 330 is disposed within the handle 318 adjacent the power source 332).

The sensor(s) can be in communication with neural and myo monitoring systems known in the art. For example, the sensor(s) can be configured to monitor conductivity of the contacted tissue in order to sense when neural tissue is near and/or when the adjacent neural tissue is active. The sensor(s) can be coupled to the illumination source coupled to the shaft for illuminating tissue, or to a separate illumination source or other indicator provided elsewhere on the device, e.g., on the handle. When a parameter monitored by the sensor is outside of a preset range, the illumination source can alert the surgeon, for instance by flashing, blinking, turning off, or changing color when the temperature of the tissue is outside of a desired range. To achieve this communication between the sensor and the illumination source, the sensor and illumination source can be electrically coupled in a circuit that is housed within the device, or that includes components that are external to the device (such as an external signal processor).

Figure 8A:
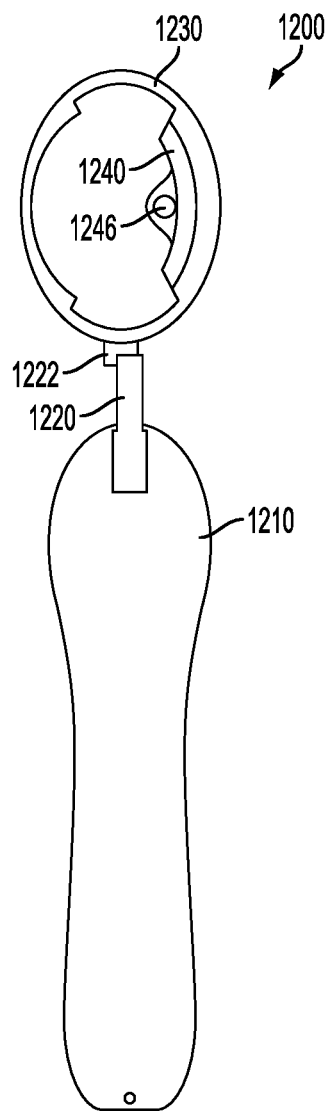
FIG. 8A is a top view of one embodiment of a retractor including a modular ring retractor.
Figure 8B:
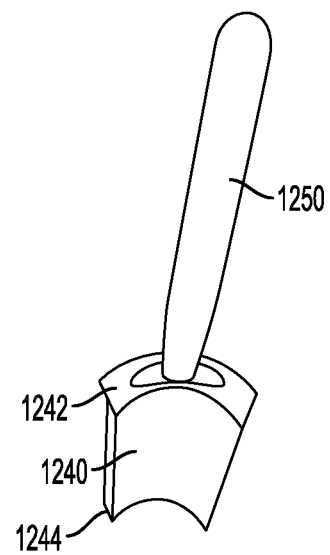
FIG. 8B is a perspective view of one embodiment of a removable blade for use with the ring retractor of FIG. 8A.

FIGS. 8A-8C illustrate another embodiment of a tissue retractor. The retractor 1200 can include a handle 1210 and an elongate shaft 1220 extending distally from the handle 1210. The retractor 1200 can also include a support ring 1230 coupled to a distal end 1222 of the elongate shaft. The support ring 1230 can be configured to removably mate to a plurality of blades 1240. As shown, the ring 1230 can have an oblong or oval shape. Alternatively, the ring can have a circle, pentagon, octagon, or any other geometric shape. One or more blades 1240 can be mated to the support ring 1230 to retract tissue surrounding the blades 1240.

FIG. 8B illustrates one of the removable blades 1240 in more detail. The blade 1240 can have proximal and distal ends 1242, 1244. The distal end 1244 can be configured to be disposed in and to retract tissue. The proximal end 1242 can be configured to snap into the support ring 1230. While the blades 1240 can be removably attached to the ring 1230 using various techniques, in one embodiment a snap-fit engagement can be utilized. For example, the blade can include an elongate surface protrusion (not shown) extending laterally across a proximal end 1242 thereof, and the ring 1230 can include an elongate groove (not shown) that is configured to seat and engage the protrusion on the blade 1240.

FIG. 8B further illustrates an insertion handle 1250 that can be connected to the proximal end 1242 of the blade 1240 and that can be manipulated to twist the blade 1240 into engagement within the ring 1230. Such a configuration can allow the blades 1240 to be attached to the ring 1230 intraoperatively. As further shown in FIG. 8A, the blade 1240 can have an aperture 1246 form on an inwardly facing surface thereof that can be designed to receive a bone anchor or other surgical implement.

FIG. 8C illustrates the exemplary retractor 1200 having three blades 1240, 1240', 1240'' snapped into place in the support ring 1230 in a configuration that will retract tissue and define a deep access portal or cavity in tissue. As shown, the ring 1230 need not have blades 1240, 1240', 1240'' mated in a full circle around the ring 1230, rather, a portion of the ring 1230 can be free of blades 1240 as shown. Additionally, any one or more of the ring 1230, the blades 1240, 1240', 1240'', and elongate shaft 1220 can include an illumination source disposed thereon or therein to illuminate the deep access portal or cavity created by the system, and/or a sensor as described herein to monitor at least one parameter of the retracted tissue.

Figure 9:
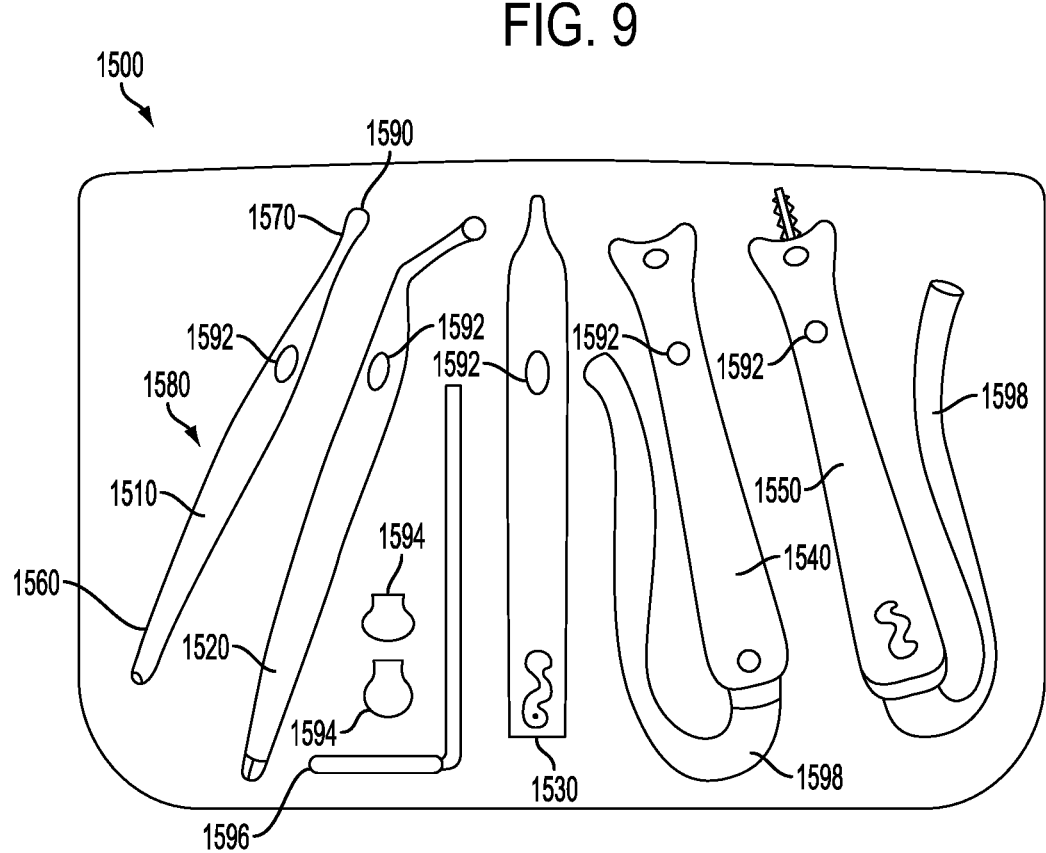
FIG. 9 is a top view of one embodiment of a surgical kit.

FIG. 9 illustrates an exemplary surgical kit 1500 for retracting tissue. An exemplary kit 1500 can include any tools necessary for performing any type of surgery, such as spinal surgery, and in particular thoracic surgery. As shown, the kit 1500 can include a combination of devices, such as illuminating retractors 1510, 1520, 1530, 1540, 1550. With reference to retractor 1510, each illuminating retractor can have a proximal end 1560, a distal end 1570, and an elongate intermediate portion 1580. The distal end 1570 can have a retraction tip 1590 and a sensor (not shown) disposed thereon to monitor at least one physiological parameter of a body tissue. The elongate intermediate portion 1580 can include an illumination source 1592 as described herein to illuminate an area surrounding the distal end. A person skilled in the art will appreciate that the kit can include any combination of retractors having any combination of features disclosed herein.

The kit can also include one or more modular tips 1594 configured to be removably disposed over any one of the blunt retracting tips on retractors 1510, 1520, 1530, 1540, 1550. Each modular tip can be in the form of a cap having a shape that is different from the shape of the other modular tips and the shape of the retractor tips so as to allow the tip of the retractor to be modified as may be desired based on the intended use. The tips can be of a different material such as absorptive polymer/sponge/cloth 1594. This can allow the retractor blade to perform various other functions, such as the function of a Kittner dissector. The kit can further include at least one support ring 1596 configured to support one or more of the retractors 1510, 1520, 1530, 1540, 1550 at the proximal end of a retractor when the retractor 1510, 1520, 1530, 1540, 1550 is disposed within the body. For example, proximal end 1560 of retractor 1510 can be configured to mate to the support ring 1596. Some of the retractors, e.g., retractors 1540 and 1550, can include a malleable connector 1598 extending from a proximal end thereof that is configured to be wrapped around the ring for mating the retractor to the support ring.

A person skilled in the art will appreciate that the systems and devices disclosed herein can be formed of any known biologically compatible material that is suitable for the given component's described properties, function, and design. For example, the elongate retraction shaft, support ring, and blades can be formed of any biocompatible rigid or semi-rigid material, such as stainless steel, nitinol, platinum, tungsten, polytetrafluorethylene (PTFE), polyamides, polyethers, polyurethanes, polyvinylchloride, silicones, and various other metals, metal alloys, polymers, and copolymers known to those skilled in the art to have the desired mechanical properties. The blunt retraction tip can be formed from the same or different materials as the elongate retraction shaft and can include various coatings to provide additional beneficial material properties. For example, the tip can have a low-durometer coating, such as silicone or Teflon. The handle can also have a coating thereon, for instance a non-conductive, non-slip coating such as rubber or silicone.

Figure 10:
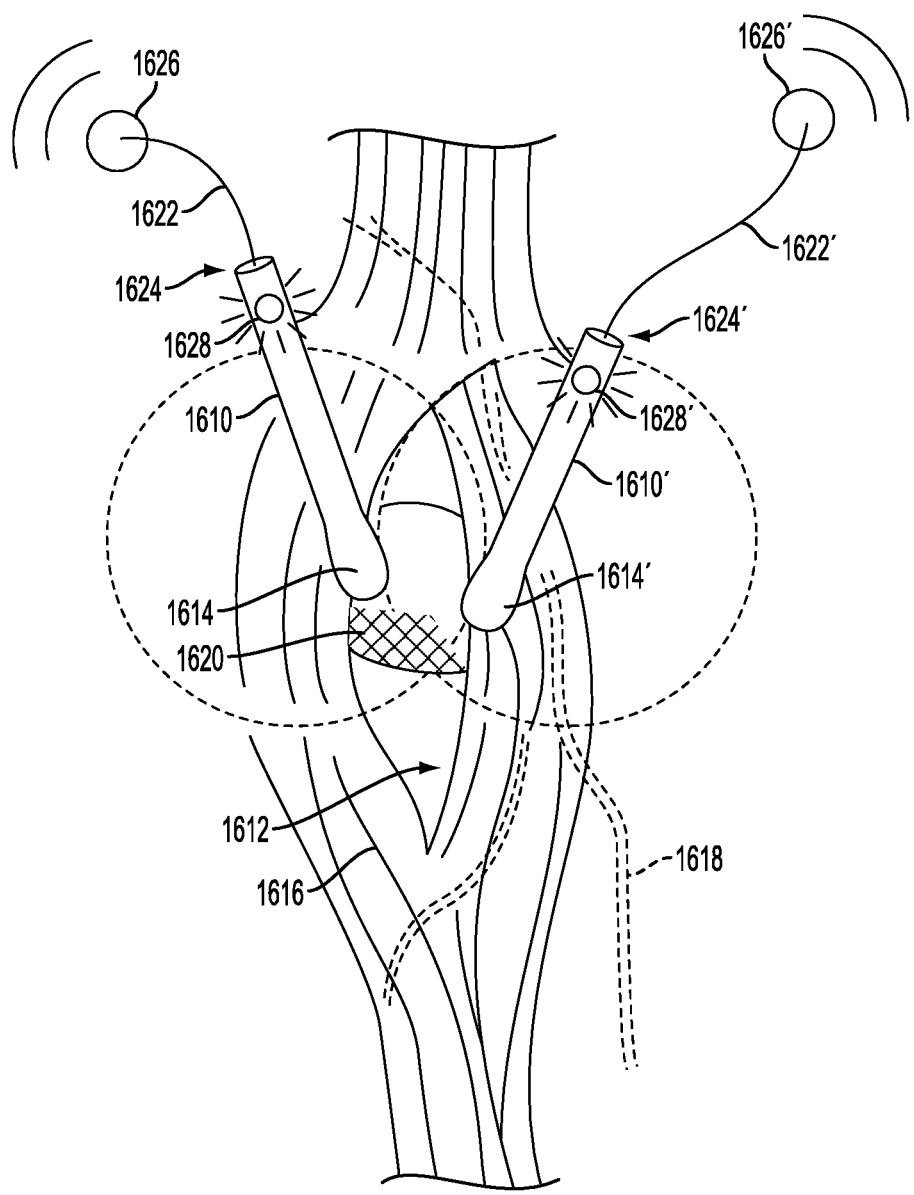
FIG. 10 is a perspective view of one embodiment of a tissue retractor disposed within a deep access portal.

FIG. 10 illustrates one exemplary use of a tissue retractor. In this embodiment, two retractors 1610, 1610' are placed within a deep access portal 1612 in a body and are configured to manipulate tissue. Manipulating tissue can include separating, retracting, distracting, dilating, or otherwise moving tissue within the body. Manipulating can also include cutting or severing tissue, such as with a beveled knife blade (not shown), or alternatively can include retracting and distracting tissue without cutting the tissue, for example with a blunt retraction tip 1614, 1614'. The devices can hold muscle 1616 and nerve fibers 1618 away from the portal 1612 thus giving access to the underlying bone 1620 and preventing the sensitive neural 1618 and muscular tissues 1616 from being unnecessarily contacted during procedures involving the bone.

The devices 1610, 1610' are shown in cut-away with the internally powered handles and surgeon's hands represented by 1626 and 1626'. Alternatively the devices can include connectors 1622, 1622' extending from a proximal end 1624, 1624' of the devices 1610, 1610'. The connectors can be coupled to an external power supply or signal processor (not shown) in the location of 1626, 1626'. The external power supply or signal processor can be configured to power or otherwise communicate with the illumination sources 1628, 1628' and/or with one or more sensors (not shown) disposed on the devices 1610, 1610'.

Figure 11:
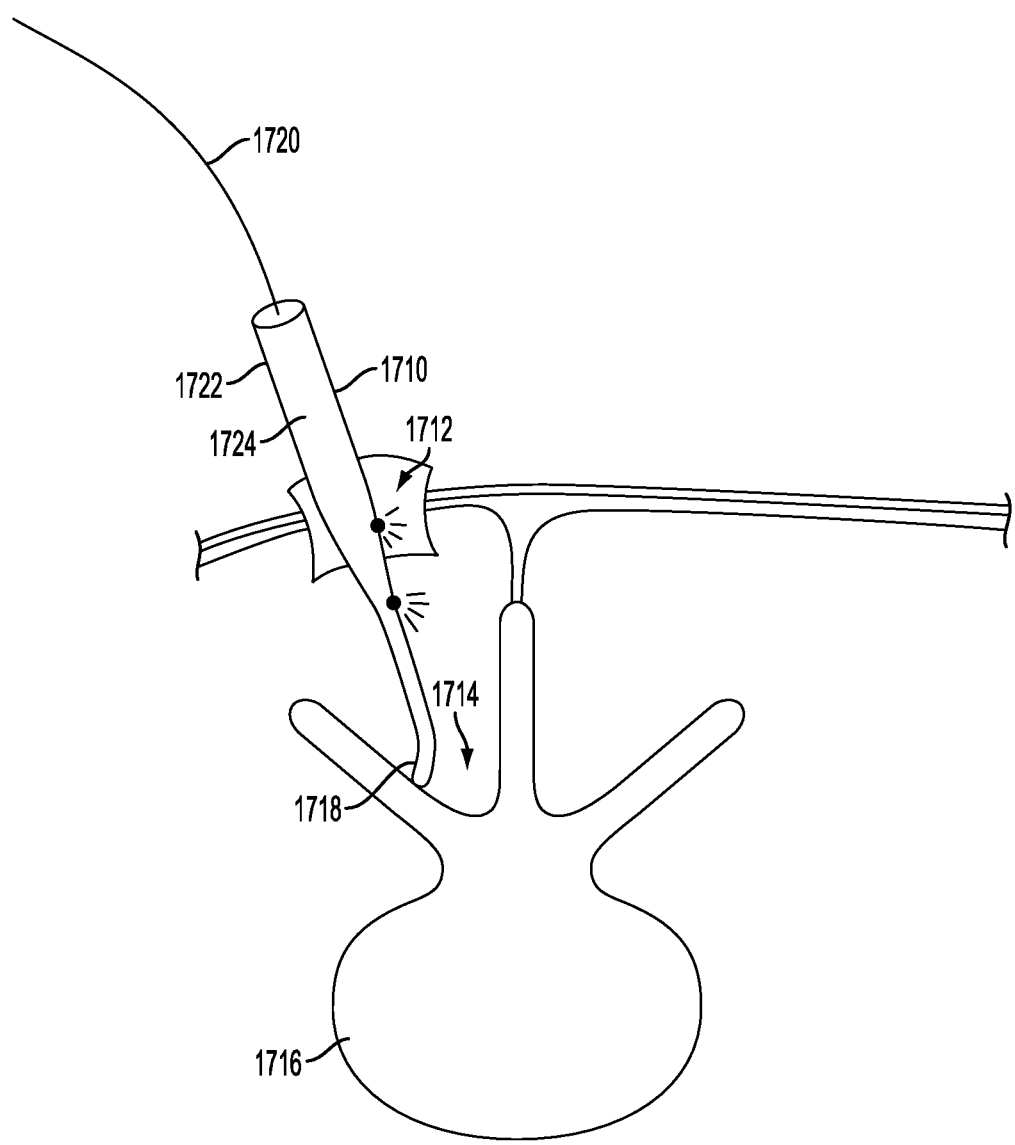
FIG. 11 is a cross-sectional view of one embodiment of a tissue retractor disposed in a body.

FIG. 11 illustrates another embodiment of a retractor 1710 disposed within a cannula 1712 defining an access portal through tissue. The surgical field 1714 can be the area near the thoracic region of the spinal column 1716 that is dense with nerve fibers. A distal tip 1718 of the retractor 1710 can be used to retract tissue to form a cavity giving access to the surgical field 1714. The retractor can include a connector 1720 extending from the proximal end 1722 of the retractor 1710 that includes a handle portion 1724.

Figure 12:
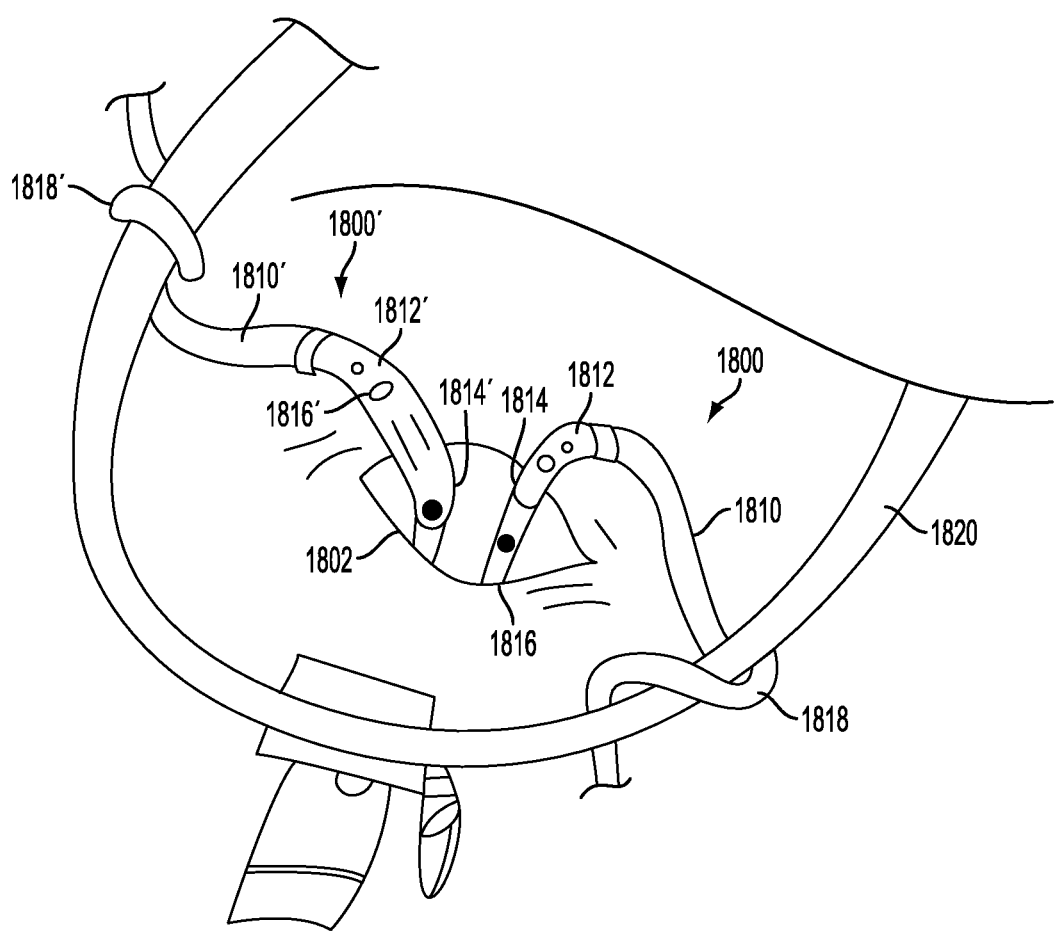
FIG. 12 is a perspective view of two malleable retractors disposed within a deep access portal and coupled to a support structure, according to another embodiment.

FIG. 12 illustrates retractors 1800, 1800' disposed in a deep access portal 1802 with connectors 1810, 1810' extending from a proximal portion 1812, 1812' of the elongate retraction shafts 1814, 1814'. The connectors 1810, 1810' can be configured to be operatively coupled, i.e., electrically, optically, and/or physically, to the proximal end 1812, 1812' of the elongate retractor shafts 1814, 1814'. The connectors 1810, 1810' can be configured to electrically connect at least one of the illumination source 1816, 1816' and a sensor (not shown) to an external signal processor such as a myo monitor. All or a portion of each connector 1810, 1810' can also be malleable 1818, 1818' to allow the connectors to wrap around and mate to a support structure 1820.

Figure 13:
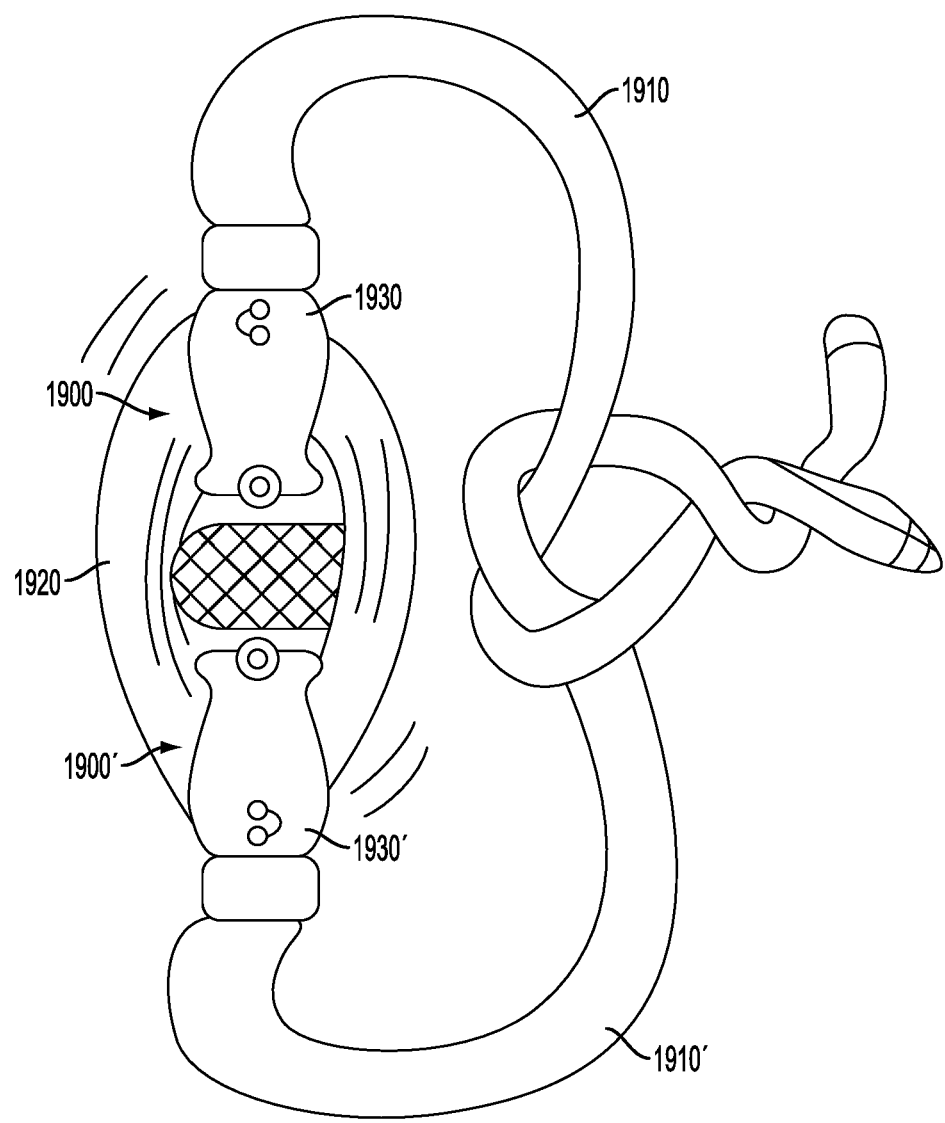
FIG. 13 is a perspective view of two malleable retractors disposed within a deep access portal and coupled to one another, according to another embodiment.

FIG. 13 illustrates another embodiment showing malleable connectors 1910, 1910' on two retractors 1900, 1900' tied or otherwise coupled to one another such that when the retractors 1900, 1900' disposed within a body 1920, they are maintained in a stable position. As with the previous embodiment, the connectors 1910, 1910' can be formed of any known articulatable and/or malleable wire or sheath. For example, the connectors 1910, 1910' can be a segmented, articulatable sheath with a conductive wire or fiber optic cable running therethrough to electrically or fiber optically connect the device to an external system. The connectors 1910, 1910' can thus mate to the proximal end 1930, 1930' of the retractors 1900, 1900' and can extend through a lumen in the device to make an electrical connection with at least one of the illumination source and the sensor.

A person skilled in the art will appreciate that the present disclosure has application in conventional minimally-invasive and open surgical instrumentation as well application in robotic-assisted surgery. The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method for manipulating tissue in a surgical field, comprising:
    inserting an elongate retractor shaft into the surgical field, the elongate retractor shaft includes a lumen extending at least partially through the elongate retractor shaft;
    delivering a surgical accessory or tool through a second lumen in the elongate retractor shaft;
    manipulating tissue in the surgical field with a distal retraction tip of the elongate retractor shaft without appreciably severing the tissue;
    monitoring at least one physiological parameter of tissue in or adjacent to the surgical field with a sensor disposed on the retraction tip; and
    illuminating at least a portion of the surgical field with an illumination source disposed on the elongate retractor shaft when the parameter monitored by the sensor is outside a preset range.

2. The method of claim 1, wherein inserting the elongate retractor shaft into the surgical field further comprises inserting the elongate retractor shaft into a deep access portal in a body of a patient.

3. The method of claim 1, further comprising delivering power from an internal power source to at least one of the illumination source and the sensor, wherein the internal power source is disposed within a handle portion of the elongate retractor shaft.

4. The method of claim 1, further comprising delivering power from a power source to a signal processor located within the elongate retractor shaft; and
    delivering power from the signal processor to at least one of the illumination source and the sensor.

5. The method of claim 1, further comprising anchoring the distal retraction tip into a bone in the surgical field.

6. The method of claim 1, wherein monitoring at least one physiological parameter of tissue further comprises sensing at least one of a temperature, a pressure, a blood oxygen level, neuro conductivity, or combinations thereof.

7. The method of claim 1, further comprising displaying an output of the sensor on a display disposed on a handle portion of the elongate retractor shaft.

8. A method of monitoring tissue in a surgical field, comprising:
    inserting a retractor into the surgical field, the retractor having a handle portion on a proximal end of an elongate shaft and a retraction tip on a distal end of the elongate shaft, the retraction tip having a distal-facing concave end;
    coupling a malleable connector of the retractor to a second retractor such that the retractor and the second retractor are disposed in a stable position;
    manipulating tissue in the surgical field with the retraction tip;
    sensing at least one physiological parameter of the tissue using a sensor disposed on the retraction tip; and
    activating an illumination source disposed in the retraction tip when a parameter sensed by the sensor is outside a preset range.

9. The method of claim 8, further comprising contacting tissue or bone within the surgical field with the concave end of the retraction tip.

10. The method of claim 8, further comprising mating the retractor to a support structure.

11. The method of claim 10, wherein mating the retractor to the support structure further comprises wrapping a malleable connector of the retractor around the support structure.

12. The method of claim 8, wherein activating the illumination source further comprises activating a plurality of illumination sources.

13. A method of sensing physiological parameters of tissue in a surgical field, comprising:
    inserting an elongate retractor shaft into the surgical field, the elongate retractor shaft having a handle portion located on a proximal end of the elongate shaft and a retraction tip disposed on a distal end of the elongate shaft, the elongate retractor shaft includes a lumen extending at least partially through the distal end of the elongate retractor shaft;
    delivering a surgical accessory or tool through a second lumen in the elongate retractor shaft;
    manipulating tissue with the retraction tip;
    sensing a physiological parameter of the tissue using a sensor disposed on the retraction tip, the physiological parameter selected from a group consisting of temperature, blood oxygen level, neural conductivity, and combinations thereof; and
    activating an illumination source when the sensed parameter is outside a preset range.

14. The method of claim 13, further comprising monitoring neural conductivity of the tissue.

15. The method of claim 14, wherein monitoring the neural conductivity of the tissue includes sensing a presence of neural tissue.

16. The method of claim 14, wherein monitoring the neural conductivity of the tissue includes sensing when adjacent neural tissue is active.

17. The method of claim 13, wherein sensing the physiological parameter of the tissue includes monitoring real-time data.

18. The method of claim 13, wherein the lumen extends into at least one aperture formed at a convex surface of the elongate retractor shaft, and
    wherein activating the illumination source includes activating an illumination source disposed in the at least one aperture.

19. The method of claim 13, further comprising contacting the tissue with the distal end of the retraction tip and sensing the physiological parameter of the contacted tissue.

\* \* \* \* \*